United States Patent
Delarche et al.

(10) Patent No.: US 7,205,372 B2
(45) Date of Patent: Apr. 17, 2007

(54) FUNCTIONALIZATION OF SILICONES AND ANTI-ADHESIVE COATINGS MADE THEREFROM

(75) Inventors: Jean-Pierre Delarche, Lachassagne (FR); Stefan Breunig, Villette de Vienne (FR); Sebastien Sterin, St-Cyr au Mont d'Or (FR)

(73) Assignee: Rhodia Chimie, Aubervilliers (FR)

( * ) Notice: Subject to any disclaimer, the term of this patent is extended or adjusted under 35 U.S.C. 154(b) by 239 days.

(21) Appl. No.: 10/933,542

(22) Filed: Sep. 3, 2004

(65) Prior Publication Data

US 2005/0075251 A1 Apr. 7, 2005

Related U.S. Application Data

(63) Continuation of application No. PCT/FR03/02650, filed on Sep. 5, 2003.

(60) Provisional application No. 60/501,014, filed on Sep. 9, 2003.

(51) Int. Cl.
C08G 77/08 (2006.01)

(52) U.S. Cl. .................... 528/15; 528/25; 528/27; 528/31

(58) Field of Classification Search .............. None
See application file for complete search history.

(56) References Cited

U.S. PATENT DOCUMENTS

| | | | |
|---|---|---|---|
| 3,775,452 A | 11/1973 | Karstedt | |
| 4,083,856 A * | 4/1978 | Mendicino | 549/215 |
| 4,398,010 A * | 8/1983 | Adkins | 528/15 |
| 4,804,768 A | 2/1989 | Quirk et al. | |
| 5,258,480 A | 11/1993 | Eckberg et al. | |
| 5,260,399 A | 11/1993 | Crivello et al. | |
| 5,391,676 A | 2/1995 | Eckberg et al. | |
| 5,623,026 A * | 4/1997 | Buekers et al. | 525/463 |
| 6,365,696 B1 | 4/2002 | Westmeyer et al. | |
| 7,038,001 B2 | 5/2006 | Breunig et al. | |

FOREIGN PATENT DOCUMENTS

| EP | 0 262 642 A | 4/1988 |
|---|---|---|
| EP | 0 415 243 A2 | 3/1991 |
| EP | 0 574 264 A2 | 12/1993 |
| EP | 0 574 265 A2 | 12/1993 |
| EP | 0 578 354 B | 1/1994 |
| EP | 0 605 143 A | 7/1994 |
| WO | WO 97/47677 | 12/1997 |

* cited by examiner

Primary Examiner—Marc S. Zimmer
(74) Attorney, Agent, or Firm—Buchanan, Ingersoll & Rooney PC

(57) ABSTRACT

Organosilicon compounds having at least one $\equiv$SiH unit per molecule are functionalized via heterogeneous catalysis into, for example, epoxidized POS by hydrosilylation between an ethylenically unsaturated epoxide such as VCMX and a hydrogenated POS of the MDD'M type with $M=R_3SiO_{1/2}$, $D=R_2-SiO_{2/2}$, $D'=RH=SiO_{2/2}$, in which R=alkyl, and wherein the viscosity of the final product is controlled, i.e., to limit the parasitic reactions of cationic polymerization by opening of heterocycles, resulting in partial or total gelling of the reaction mixture, said hydrosilylation characteristically being carried out in the presence of at least one inorganic non-nucleophilic base and, optionally, water.

13 Claims, No Drawings

FUNCTIONALIZATION OF SILICONES AND ANTI-ADHESIVE COATINGS MADE THEREFROM

CROSS-REFERENCE TO PRIORITY/PROVISIONAL APPLICATIONS

This application claims priority under 35 U.S.C. § 119 of PCT/FR-03/02650, filed Sep. 5, 2003 and of provisional application Ser. No. 60/501,014, filed Sep. 9, 2003, each hereby expressly incorporated by reference and each assigned to the assignee hereof. This application is also a continuation of said PCT/FR 03/02650 and of said '014 provisional.

BACKGROUND OF THE INVENTION

1. Technical Field of the Invention

The present invention relates to the production of functionalized organosilicon compounds. These organosilicon compounds are in particular organosilanes and polyorganosiloxanes (POS), onto which functional radicals, such as, for example, radicals carrying at least one epoxy function, are grafted.

2. Description of Background and/or Related and/or Prior Art

One objective of the functionalization of silicones formed by POS oils is to improve their ability to attach to supports made of paper or the like, of polymer, of glass or of metal. Thus, epoxy-functionalized silicone oils are of advantageous use as anti-adhesive coatings for flexible supports, for example made of paper or of polymer film, or as lubricants.

The grafting of such functional radicals is carried out using precursors which may be of the type of those carrying at least one site of unsaturation, preferably ethylenic unsaturation, capable of reacting with ≡Si—H units belonging to an organohydrosilane and/or a hydrogenated POS. The silicone oils involved are, for example, those of formulae:

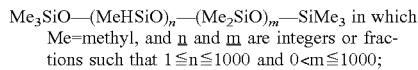
Me=methyl, and $n$ and $m$ are integers or fractions such that $1 \leq n \leq 1000$ and $0 < m \leq 1000$;

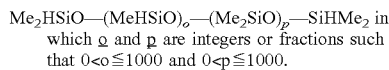
which $o$ and $p$ are integers or fractions such that $0 < o \leq 1000$ and $0 < p \leq 1000$.

Many synthons can functionalize polyorganohydrosiloxanes; for example, alkenes, styrenes, allyl alcohols, allyloxy ethers or allylamines are used as synthons.

The hydrosilylation reaction is conventional in the field of the functionalization of silicone compounds, and in particular of POS. It is catalyzed, in homogeneous or heterogeneous phase, by organometallic catalysts, in particular based on transition metals (for example, Karstedt: U.S. Pat. No. 3,775,452 B).

A problem exists which is related to the use of organometallic catalysts such as platinum for the hydrosilylation of ethylenically unsaturated reagents bearing heterocycles (e.g., epoxy), with ≡Si—H units carried by organosilicon compounds such as silicone oils.

In fact, these platinum catalysts for hydrosilylation have the unwanted side effect of promoting opening of the heterocycles, which generates parasitic polymerization/crosslinking involving many heterocyclic functions (in particular epoxides) and which can sometimes result in complete gelling of the reaction medium (formation of gums or of resins). Under these conditions, it is very difficult to obtain final products, namely functionalized organosilicon compounds (silicones), having a completely controlled viscosity. Such a difficulty is particularly harmful for functionalized silicone oils intended for applications such as anti-adhesive coatings.

By way of illustration of this undesirable property that platinum catalysts have of cleaving heterocycles, mention may be made of EP-A-0,415,243, the aim of which is precisely to exploit this property of platinum catalysts for the polymerization of heterocyclic compounds such as epoxy-functional silicones, epoxy-functional acrylic polymers, and also monomers chosen from the group comprising tetrahydrofurans, oxetanes, lactones, spirocarbonates, spiro esters, sulfur-containing cyclic compounds and nitrogenous cyclic compounds.

Various technical propositions have come to the fore in an attempt to solve this problem.

Among them, it is possible to distinguish those involving homogeneous organometallic catalysts and those concerning heterogeneous catalytic systems. As regards the technical propositions in homogeneous phase presented as preventing the opening of the heterocyclic functions, in particular epoxides, of the ethylenic precursors for grafting onto silicones containing ≡SiH units, mention may be made of U.S. Pat. No. 5,258,480 B which discloses a process for preparing epoxy-functional silicones by means of a catalytic complex for hydrosilylation based on rhodium {RhCl₃[(CH₃(CH₂)₃)₂S]₃;PtCl₂[(CH₃CH₂)₂S]₂} in homogeneous phase and in the presence of a stabilizer consisting of a tertiary amine [CH₃(C₁₈H₃₇)₂N].

U.S. Pat. No. 5,260,399 B concerns the synthesis of epoxysiloxane monomers and polymers by hydrosilylation in the presence of a homogeneous catalyst comprising a phosphine ligand and a complex based on a transition metal (platinum, palladium, rhodium, iridium, iron or cobalt) and not containing phosphine.

EP-A-0,574,265 concerns a process for preparing an epoxysilicone composition that is crosslinkable by hydrosilylation of an ethylenically unsaturated epoxide, using a silicone containing ≡Si—H units in the presence of a homogeneous catalyst for hydrosilylation containing rhodium of formula:

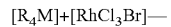

in which M=P or N and R=C$_{1-18}$ organic radical.

EP-A-0,574,264 relates to the synthesis of epoxysilicones by hydrosilylation of an ethylenically unsaturated epoxide using a silicone containing ≡Si—H units, in the presence of a homogeneous catalyst of the type quaternary ammonium, phosphonium or arsonium hexahaloplatinate of formula:

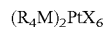

in which M=As, P or N; X=halogen and R=C$_{1-30}$ organic radical.

None of these homogeneous-phase technical propositions provide satisfactory solutions to the technical problem under consideration. In addition, they have the disadvantages of homogeneous-phase reactions. Thus, the functionalized silicone oils obtained from processes using homogeneous catalysis are generally colored, of the order of 120 to 300 hazen; which consequently limits the fields in which their use can be envisioned, in particular in the field of transparent and anti-adhesive films for paper or for transparent films (for example of polyester type). This coloration is generally due to the presence, in the functionalized oils, of metal aggregates or of colloids of nanometric size, derived from the homogeneous catalytic compositions used in the hydrosilylation processes of the prior art. In these cases, the silicone oil requires additional steps of filtration and purification so that it can be usable after crosslinking in the field of transparent films; these supplementary steps make industrial implementation expensive and therefore relatively nonviable in economic terms.

Finally, the catalytic complexes used in these propositions have the disadvantage of being expensive.

In order to be free of the problems associated with homogeneous catalysis, WO-A-97/47677 proposes a heterogeneous organometallic catalysis for obtaining epoxy functionalized silicone oils free of any organometallic residues after filtration. This process for preparing epoxy silicone oils which are weakly colored and low in turbidity by hydrosilylation of hydrogenated POS with unsaturated and epoxidized synthons, in the presence of a metal (platinum) deposited on an inert support, gives relatively satisfactory results in terms of control of the cationic polymerization by opening of the epoxide rings and therefore of the gelling and the viscosity of the final product.

However, this heterogeneous organometallic catalysis can still be perfected, especially in the particular case of 4-vinylcyclohexene epoxide (VCMX).

More recently, U.S. Pat. No. 6,365,696 B disclosed a process for preparing epoxidized POS, according to a platinum-catalyzed process of hydrosilylation between an ethylenically unsaturated epoxide such as VCMX and a hydrogenated POS of the MDD'M type with $M=R_3-SiO_{1/2}$, $D=R_2-SiO_{2/2}$; $D'=RH-SiO_{2/2}$, in which R=alkyl; in the presence of platinum (chloroplatinic acid solution), of a carboxylic acid salt (sodium propionate) and, optionally, of a promoter for the catalyst, namely an alcohol or a carboxylic acid. The alcohol may be propylene glycol or tetraethylene glycol. Sodium carbonate may be used to treat the VCMX. It should be noted that the process according to that patent is used in the absence of water.

SUMMARY OF THE INVENTION

The present invention features a process for synthesizing functionalized organosilicon compounds, in particular POS silicone oils functionalized with heterocycles such as epoxides, by heterogeneous catalysis, making it possible to control, in an optimized manner, the viscosity of the final product, i.e., to limit the parasitic reactions of cationic polymerization by opening of heterocycles resulting in partial or total gelling of the reaction mixture.

The present invention also features a process for synthesizing organosilanes and/or POS functionalized with heterocycles, and in particular epoxy-functionalized, according to a hydrosilylation process involving a heterogeneous catalyst, in a reliable and reproducible manner.

This invention also features a process for synthesizing organosilanes and/or POS functionalized with heterocycles, and in particular epoxy-functionalized, according to a hydrosilylation process involving a heterogeneous catalyst, which makes it possible to very significantly reduce the coloration within the unsaturated synthon.

This invention also features a process for synthesizing organosilanes and/or POS functionalized with heterocycles, and in particular epoxy-functionalized, according to a hydrosilylation process involving a heterogeneous catalyst, making it possible to obtain a wide range of functionalized silicone oils while at the same time controlling the viscosity of the final product in a stable manner, avoiding any gelling.

The present invention also features a process for synthesizing organosilanes and/or POS functionalized with heterocycles, and in particular epoxy-functionalized, according to a process of hydrosilylation involving a heterogeneous catalyst, in a simple and economical manner.

This invention also features a process for synthesizing organosilanes and/or POS functionalized with heterocycles, and in particular epoxy-functionalized, according to a process of hydrosilylation involving a heterogeneous catalyst, the organosilicon compounds obtained being weakly colored and low in turbidity, without resorting to too laborious a process of filtration or purification.

This invention also features a process for synthesizing organosilanes and/or POS functionalized with heterocycles, and in particular epoxy-functionalized, according to a process of hydrosilylation involving a heterogeneous catalyst, the functionalized silane or silicone products obtained having a low viscosity, for example less than or equal to 50 mpa.s at 25° C., for the products obtained from tetramethylhydrodisiloxane ($M'_2$).

The present invention also features organosilicon compounds functionalized with radicals carrying heterocycles, in particular epoxides, which are barely, if at all, polymerized/crosslinked by opening of heterocycles.

The present invention also features epoxy functionalized POS silicone oils of low and controlled viscosity, which are varied in nature, barely, if at all, cloudy, barely, if at all, colored, economical, stable and simple to obtain.

This invention also features an anti-adhesive silicone varnish, ink or coating which attaches well to any type of support and which comprises epoxy functionalized oils having the abovementioned qualities, in particular the fluidity.

The present invention thus features, first of all, a process for functionalizing at least one organosilcon compound carrying at least one ≡SiH unit per molecule, by hydrosilylation of at least one synthon including at least one site of unsaturation (preferably ethylenic unsaturation) containing at least one heterocycle in which the hetero atom is preferably oxygen, said hydrosilylation being carried out in the presence of a heterogeneous catalytic composition comprising at least one metal which is selected from the group consisting of cobalt, rhodium, ruthenium, platinum and nickel, and which is deposited on an inert support, and further wherein the hydrosilylation is carried out in the presence of at least one inorganic non-nucleophilic base and, optionally, water.

DETAILED DESCRIPTION OF BEST MODE AND SPECIFIC/PREFERRED EMBODIMENTS OF THE INVENTION

More particularly according to the present invention, it has now been demonstrated that the addition of an inorganic non-nucleophilic base (in particular of hydrogen carbonate type) together with the supported hydrosilylation catalyst and, optionally, in the presence of water, makes it possible to prepare, in a reliable, reproducible, simple and economical manner, functional silicone oils that are particularly advantageous, in particular in terms of viscosity, which is advantageously low and controlled.

This method of synthesis by heterogeneous catalysis makes it possible to obtain transparent and fluid functionalized silicone oils which are perfectly suitable for producing anti-adhesive coatings, in particular on paper or polymer film, obtained after cationic crosslinking under thermal and/or actinic (UV) activation.

For the purpose of the present disclosure, the term "heterogeneous catalytic composition" denotes a catalytic composition which may be solid or liquid, and which is not dissolved in the reaction medium, i.e., the reaction medium comprises at least two phases, one of which is formed by the catalytic composition.

According to a preferred embodiment, the inorganic non-nucleophilic base is selected from the group consisting of hydrogen carbonates or carbonates or alkali metals (preferably of sodium or of potassium), phosphates of alkali metals (preferably of sodium or of potassium), sulfates of alkali metals (preferably of sodium or of potassium) and mixtures thereof.

It may, for example, be $H_2PO_4Na$, $HPO_4Na_2$, $Na_2CO_3$, $NaHCO_3$, $KNCO_3$.

In other words, the inorganic non-nucleophilic base should have a pKA such that, at the concentrations for use below 5%, the pH of the medium is advantageously between 6 and 12, preferably between 4 and 9.

By virtue of these advantageous arrangements, the invention makes it possible to obtain functionalized (e.g., epoxidized) silicone oils which have a low viscosity and which have undergone a loss of functions (e.g., epoxides) less than 20% in number.

According to a preferred embodiment of the invention, the functionalization process comprises at least one devolatilization step, carried out after the hydrosilylation and in the presence of at least one inorganic non-nucleophilic base.

This devolatilization step is advantageously carried out after removal of the catalytic system by filtration. It is intended to remove the light compounds from the reaction medium. The advantage of using at least one inorganic non-nucleophilic base at this stage is in particular that it results in products which are barely, if at all, colored and which are of lower viscosity.

In quantitative terms, it appeared to be preferable, during the hydrosilylation or the devolatilization, to use an amount of inorganic non-nucleophilic base of between 1 and 10,000 ppm, preferably between 10 and 5,000, and even more preferably between 100 and 4,000, relative to the total mass of synthon and of organosilicon compound.

According to a preferred embodiment of the invention, the water is a reaction auxiliary, present during the hydrosilylation in an amount of less than or equal to 5%, preferably of between 500 and 5,000 ppm, relative to the total mass of synthon and of organosilicon compound.

This water significantly contributes to the performance levels of the heterogeneous catalyst in terms of limited losses of functionalization grafts, and therefore of reduced viscosity.

This water can be initially present in the reaction medium and/or can be added subsequently in the course of the process.

It can be introduced into the reaction medium directly or indirectly, by means of the products used. Thus, the catalyst may, for example, be hydrated and contain 50% of water.

The metal of the catalytic composition is preferably platinum.

The amount of metal contained in the heterogeneous catalytic composition ranges from 0.005% to 5% relative to the weight of the inert support. This amount of metal also ranges from 1 to 1,000 rpm relative to the weight of the silicone oil.

The metal is deposited on varied inert supports, such as carbon black, charcoal, alumina, treated or untreated silica, barium sulfate, or else crosslinked silicones. Advantageously, the mean particle size of the catalytic supports is greater than 10 μm in order to have good filterability which does not require filtration adjuvants. Thus, this mean particle size is such that the filtration time can be considerably reduced.

According to a notable characteristic of the invention, the synthons contain at least one hydrocarbon-based ring, included in which is an oxygen atom, and have the formula:

(1)

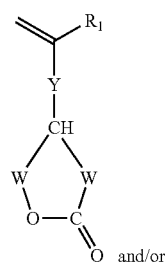

(I)

and/or

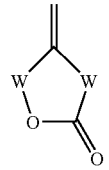

(II)

in which:
- the symbols W are identical or different and correspond to a divalent hydrocarbon-based radical selected from among linear or branched alkylene radicals having from 1 to 12 carbon atoms, with the proviso that one of the symbols W may be a free valency;
- the symbol Y corresponds to a free valency or a divalent radical selected from among linear or branched alkylene radicals having from 1 to 12 carbon atoms and optionally containing a hetero atom, preferably an oxygen atom;
- the symbol $R_1$ corresponds to a hydrogen atom or a monovalent hydrocarbon-based radical selected from among linear or branched alkyl radicals having from 1 to 12 carbon atoms, and preferably a hydrogen atom or a methyl radical;

(2)

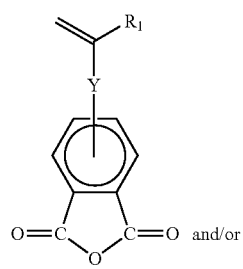

(III)

and/or

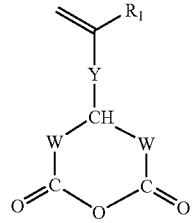

(IV)

in which:
- the symbols W are identical or different and correspond to a divalent hydrocarbon-based radical selected from among linear or branched alkylene radicals having from 1 to 12 carbon atoms, with the proviso that one of the symbols W may be a free valency;
- the symbol Y corresponds to a free valency or divalent radical selected from among linear or branched alkylene radicals having from 1 to 12 carbon atoms and optionally containing a hetero atom, preferably an oxygen atom;
- the symbol $R_1$ corresponds to a hydrogen atom or a monovalent hydrocarbon-based radical selected from among linear or branched alkyl radicals having from 1 to 12 carbon atoms, and preferably a hydrogen atom or a methyl radical;

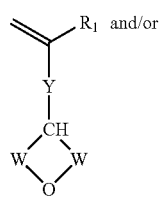
(V) and/or

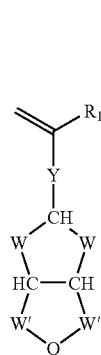
(VI)

in which
- the symbols W are identical or different and correspond to a divalent hydrocarbon-based radical selected from among linear or branched alkylene radicals having from 1 to 12 carbon atoms and optionally containing at least one hydroxyl function; with the proviso that one of the symbols W may be a free valency for (V) and the two symbols W can simultaneously be a free valency for (VI);
- the symbols W' are identical or different and correspond to a divalent hydrocarbon-based radical selected from among linear or branched alkylene radicals having from 1 to 12 carbon atoms; with the proviso that at least one of the symbols W' may be a free valency;
- the symbol Y corresponds to a free valency or a divalent radical selected from among linear or branched alkylene radicals having from 1 to 12 carbon atoms and optionally containing a hetero atom, preferably an oxygen atom;
- the symbol R' corresponds to a hydrogen atom or a monovalent hydrocarbon-based radical selected from among linear or branched alkyl radicals having from 1 to 12 carbon atoms, and preferably a hydrogen atom or a methyl radical;

and (4)

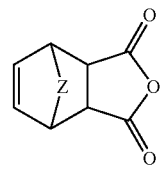
(VII)

in which:
- the symbols W are identical or different and correspond to a free valency and a divalent hydrocarbon-based radical selected from among linear or branched alkylene radicals having from 1 to 2 carbon atoms;
- the symbol Z corresponds to a divalent radical selected from a carbon atom or a hetero atom.

Preferably, the hydrocarbon-based ring in which the hydrogen atom is included comprises no more than 8 atoms in said ring. In addition, the best results in accordance with the hydrosilylation process of the invention are obtained with synthons containing only one hydrocarbon-based ring in which an oxygen atom is included. In particular, the synthons used, and which give good results (see examples below), have the formula:

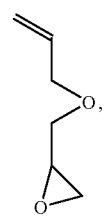
(VIII)

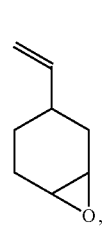
(IX)

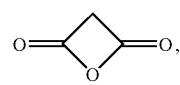
(X)

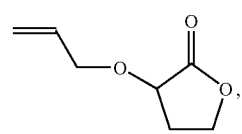
(XI)

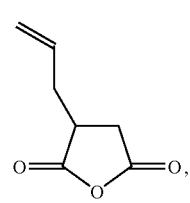
(XII)

-continued

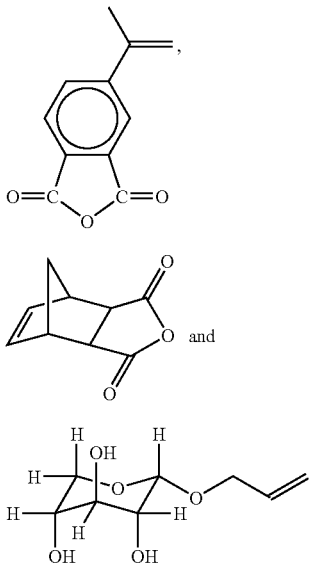

(XIII)

(XIV)

(XV)

In general, the synthons which react with the silicone oil are identical synthons. The silicone oil/synthons molar ratio ranges from 0.01 to 100, preferably from 0.1 to 10.

An accordance with the invention, the organosilicon compound containing ≡Si—H units is an epoxidized silane or an epoxidized polyorganosiloxane (POS).

The latter may be advantageously formed by a linear or cyclic silicone oil of formula corresponding to one of the average formulae below:

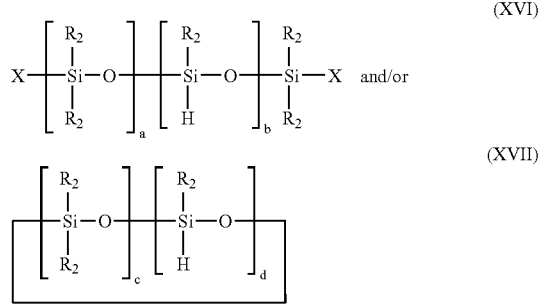

(XVI)

(XVII)

in which
the symbols $R_2$ are identical or different and correspond to a monovalent hydrocarbon-based radical selected from among the phenyl radical and linear or branched alkyl radicals having from 1 to 6 carbon atoms;
the symbols X are identical or different and correspond to a monovalent radical selected from among $R_2$, a hydrogen atom, a methoxy radical and an ethoxy radical;
a and b are integers or fractions, such that:

$0<a \leq 200$, preferably $0<a \leq 99$ $0<b \leq 200$, preferably $1<b \leq 100$, and at least one of the two X corresponding to the hydrogen radical if b=0

$5<a+b \leq 200$, preferably $10<a+b \leq 100$ c and d are integers or fractions, such that:

$0<c<5$, preferably $0<c<3$ $1<d<10$, preferably $1<d<5$ $3<a+b<10$, preferably $3<a+b<5$.

In the context of the invention, various types of heterogeneous catalytic compositions can be used.

By way of nonlimiting examples, use may be made of platinum on carbon black or charcoal, such as the catalytic composition containing 2.5% of platinum by weight deposited onto the CECA 2S support developed by the company CECA, or the catalytic composition 88 231 (1% Pt) from the company Heraeus. In this case, the platinum can be deposited onto this type of support by deposition of chloroplatinic acid followed by neutralization and reduction. Similarly, the use of platinum on alumina, preferably α-type alumina, such as the catalytic composition CAL 101 (0.3% of Pt, SCS9 support consisting of α-alumina) sold by the company Procatalyse or the catalytic composition 88 823 from the company Heraeus (0.5% of Pt on α-alumina), gives good results.

According to a notable characteristic of the invention, the silicone oil and the synthon react in the reaction medium in the absence of solvent.

The process according to the invention can be implemented according to various variants. In practice, all the reagents of the catalytic composition are mixed in the reaction medium ("batch" type).

In the context of its experimental trials, an advantageous process in accordance with the first embodiment has been developed. This process of hydrosilylation between a silicone oil and an unsaturated synthon comprises the following steps:
a) the synthon is introduced into the reaction medium;
b) an amount of 5 to 5,000 ppm, preferably of 10 to 100 ppm, of heterogeneous catalytic composition, relative to the total mass of the reagents, is introduced under inert gas into the reaction medium;
c) water is preferably introduced into the reaction medium;
d) the inorganic non-nucleophilic base (preferably sodium hydrogen carbonate) is introduced into the reaction medium;
it being possible for steps a, b, c and d to be carried out in this order or in no particular order;
e) said medium is heated to a temperature of from 25° C. to 200° C., and preferably from 50° C. to 160° C.;
f) the silicone oil is then introduced over a period of between 0 and 24 hours, preferably between 2.5 and 5 hours; the synthon/silicone molar ratio ranging from 1 to 5, preferably from 1 to 2;
g) the reaction mass is then filtered in order to separate the heterogeneous catalytic composition and the functionalized silicone oil;
h) the functionalized silicone oil is finally devolatilized in the presence of an inorganic non-nucleophilic base that may be identical or different to that mentioned above (preferably identical), and
i) the reaction mass is finally subjected to at least one operation to remove the solid residues from the reaction medium (preferably by filtration or by gravity), so as to recover the functionalized silicone oil.

This advantageous process can be carried out in bulk, which means that the reaction between the silicone oil and the synthon takes place in the absence of solvent. However, many solvents, such as toluene, xylene, octamethyltetrasiloxane, cyclohexane or hexane, can be used.

Furthermore, the molar amount of synthon introduced during step (a) is less than that which is used for a conventional process of the prior art. Advantageously, the synthon/silicone oil molar ratio ranges from 1 to 1.1, without harming the quality of the functionalized oils obtained or the yield of the reaction.

The filtration step g) makes it possible, where appropriate, to remove any trace of turbidity from the functionalized silicone oil obtained. Furthermore, the heterogeneous catalytic composition can be recovered and then re-used once more, without requiring regeneration, with or without washing, and without any substantial decrease in activity of its performance levels being noted.

The functionalized silicone oils obtained in accordance with the invention, and in particular according to the advantageous process developed, are very stable and do not undergo any modifications during the devolatilization step. Their viscosities are very substantially lower compared to those of the oils obtained from the same reagents and according to the processes of the prior art, in particular those using homogeneous catalysts.

For example, the viscosity of the oils of formula (XVI) with a=0, b=0 and X=H and $R_2$=$CH_3$, functionalized with 1,2-epoxy-4-vinylcyclohexane, obtained in the presence of $NaHCO_3$, is of the order of 20 to 30 mpa·s, which reflects the absence of opening of the rings containing an oxygen atom and therefore the absence of polymerization reactions, including during the devolatilization, due to the opening of these rings.

In addition, the oils obtained in accordance with the processes according to the invention are virtually transparent with a very weak coloration, generally less than 50 Hazen.

These oils have a very low content of metal derived from the catalytic composition, which very greatly limits the unwanted reactions that the metal could cause if the content thereof was greater. For example, in the case of oils obtained according to the invention in the presence of a catalytic composition containing in particular platinum, it is possible to mix said oils with other molecules containing ≡SiH functions and molecules containing unsaturated bonds, without risking a further hydrosilylation reaction between these molecules.

The measured epoxy content in the oils obtained according to the invention is very high and the measured epoxy content/theoretical epoxy content ratio ranges from 0.95 to 1, this theoretical epoxy content corresponding to the ≡SiH content measured on the oil before reaction.

This functionalized organosilicon compound is advantageously selected from epoxidized POS oils and/or organosilanes.

This epoxysilane or this epoxidized POS oil has the advantages of the products obtained according to the process of the invention, namely low viscosity (fluidity) suitable for the coating (at high speed) of flexible supports, in particular paper or polymer film, transparency, and also for applications as lubricants.

These functionalized products also stand out by virtue of the absence or virtual absence within them of polymers resulting from polymerization by opening of the heterocycles of the functionalization radicals.

According to another of its embodiments, the invention relates to the use of the silicone oils as defined above, as such, or through the process for obtaining them, as lubricants or for preparing anti-adhesive coatings for supports, in particular flexible supports, for example made of paper, of glass, of polymer film, in particular plastic film, or of metal.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The 4-vinylcyclohexene epoxide (VCMX) used in the examples which follow comes from the company Union Carbide. It is systematically distilled before use.

The tetramethylhydrodisiloxane ($M'_2$) used is manufactured by Rhodia Silicones. It is itself also distilled before use.

The catalyst Pt on carbon black (wet) is available from the company Aldrich under the reference 33,015-9. The platinum content is 2.5% by weight. The water content is approximately 50% by weight.

The functionalization auxiliary used is sodium hydrogen carbonate ($NaHCO_3$).

The amounts of catalyst, of $NaHCO_3$ and of water are expressed relative to the total mass of VCMX and of $M'_2$.

The epoxide functions are measured by potentiometry. The device used is a Mettler® device, model DL21, equipped with a Mettler Toledo DG 113 SC LiCl/EtOH, 1.0 M, combined electrode. The titrating solution is a solution of 0.1 N perchloric acid in acetic acid.

Common Procedure for Examples 1 to 5 and Counter-Examples 1 and 2

66 g (531 mmol=1.05 eq) of VCMX, the amount of platinum required in the form of the catalyst Pt on carbon black and, optionally, water and sodium hydrogen carbonate are loaded into a 100 ml reactor. The reaction mixture is then heated to 90° C. 34 g (506 mmol =1 eq) of $M'_2$ are then poured dropwise into the reactor over 5 h. During the synthesis, the progression of the reaction is determined by the disappearance of the ≡SiH units and the possible disappearance of the epoxy functions is followed by potentiometric measurement. When all the ≡SiH units have reacted, the reaction mixture is filtered and then devolatilized for 7 hours under vacuum at high temperature in the presence or absence of sodium hydrogen carbonate. The viscosity, which correlates directly with the loss of epoxide functions, is measured before and after devolatilization.

Procedure for Counter-Example 3

66 g (531 mmol =1.05 eq) of VCMX and the amount of platinum required in the form of the Karstedt catalyst are loaded into a 100 ml reactor. The reaction mixture is then heated to 90° C. 34 g (506 mmol=1 eq) of $M'_2$ are then poured dropwise into the reactor. The reaction mixture gels while the $M'_2$ is poured in.

Procedure for counter-Example 4

In this counter-example, functionalization of $M'_2$ with VCMX is carried out, in accordance with the teaching of U.S. Pat. No. 6,365,696, according to a process of homogeneous catalysis involving sodium acetate as catalyst.

66 g (531 mmol=1.05 eq) of VCMX, the amount of platinum required in the form of the Karstedt catalyst and the sodium acetate are loaded into a 100 ml reactor. The reaction mixture is then heated to 90° C. 34 g (506 mmol=1 eq) of $M'_2$ are then poured dropwise into the reactor over 5 h. During the synthesis, the progress of the reaction is determined by the disappearance of the ≡SiH units and the possible disappearance of the epoxy functions is followed by potentiometric measurement. When all the ≡SiH units have reacted, the reaction mixture is filtered. The viscosity, which is already high at the end of the reaction, shows that some of the epoxy functions have polymerized (loss estimated at 7.9%).

All the results obtained during the syntheses and during the devolatilizations are summarized in the table below. These examples show that this process, which includes a step comprising synthesis according to heterogeneous catalysis in the presence of a sufficient amount of water and of an inorganic non-nucleophilic base species of hydrogen carbonate type, followed by a step comprising devolatilization, preferably in the presence, here again, of a species of hydrogen carbonate type, makes it possible to obtain silicone oils of a quality that is particularly difficult to attain using another process. In particular, the processes using homogeneous catalysis leave metal residues in the medium which can degrade the quality of the product over time unless an additional step, which is often long and laborious, is carried out to remove the catalyst: sodium acetate); it shows that the use of a base which is not an inorganic non-nucleophilic base, as catalyst, gives poor results as regards the loss of epoxy and the viscosity.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for functionalizing at least one organosilcon compound carrying at least one ≡SiH unit per molecule, comprising hydrosilylating at least one synthon having at least one site of unsaturation and containing at least one heterocycle, said hydrosilylation being carried out in the

|  | Synthesis | | | | | Devolatilization | | |
|---|---|---|---|---|---|---|---|---|
|  | Added | | | | | | | |
|  | Pt (ppm) | Base (ppm) | $H_2O$ (ppm) | $t_{TTSiH=100\%}$ (hours) | Epoxy loss | Viscosity (mPa/s) | $NaHCO_3$ (ppm) | T (° C.) | Viscosity (mPa/s) |
| Ex 1 | 8 | 500 | 500 | 9 | <1% | 30 | / | 120 | 58 |
| Ex 2 | 8 | 2500 | 2500 | 9 | <1% | 26 | 1000 | 110 | 37 |
| Ex 3 | 20 | 2500 | 2500 | 7 | <1% | 27 | 2500 | 130 | 36 |
| Ex 4 | 20 | 2500 | / | 7 | 2.3% | 31 | 2500 | 130 | 42 |
| Ex 5 | 20 | 2500 | 2500 | 7 | <1% | 26 | / | 130 | 70 |
| C. Ex 1 | 8 | / | / | / | Gelling when M'$_2$ is poured in | | / | / | / |
| C. Ex 2 | 8 | 100 | 100 | (i) | 10% | 570 | Reaction mixture not devolatilized given the viscosity which is already very high at the end of synthesis | | |
| C. Ex. 3 | 20 | / | / | / | gelling when the M'$_2$ is poured in | | / | / | / |
| C. Ex 4 | 20 | 2500 | / | 7 | 7.9% | 124 | Reaction mixture not devolatilized given the viscosity which is already very high at the end of synthesis | | |

(i) reaction stopped at t = 7 h (TT$_{SiH}$ = 98.4%) given the measured epoxy loss.

Comments:

Examples 1 to 5 show that, in the presence of the inorganic nucleophilic base ($NaHCO_3$) and of water, the epoxy losses are very limited. There is therefore no undesirable polymerization/crosslinking.

It should also be noted that the viscosity of the epoxidized oils obtained in Examples 1 to 5 according to the invention is very low. This viscosity is even lower when, preferably, water is used (Examples 1 to 3 and 5).

It emerges from Examples 1 and 5 and from Examples 2 to 4 that the presence of the inorganic nucleophilic base during the devolatilization has a positive effect on limiting the increase in viscosity of the epoxy functionalized silicone, usually observed during this step.

Counter-Example 2 shows that, for a low content (100 ppm) of inorganic nucleophilic base ($NaHCO_3$), the expected results in terms of epoxy content and of viscosity are not obtained.

Counter-Example 4 corresponds to the process according to U.S. Pat. No. 6,365,696 B (homogeneous phase, basic presence of a heterogeneous catalytic composition which comprises at least one metal selected from the group consisting of cobalt, rhodium, ruthenium, platinum and nickel, and which is deposited on an inert support, and further wherein the hydrosilylation is carried out in the presence of at least one inorganic non-nucleophilic base and water, wherein said water is present during the hydrosilylation, in an amount 500 to 5,000 ppm, relative to the total mass of synthon and of organosilicon compound.

2. The process as defined by claim 1, said at least one inorganic non-nucleophilic base being selected from the group consisting of hydrogen carbonates or carbonates of alkali metals, phosphates of alkali metals, sulfates of alkali metals, and mixtures thereof.

3. The process as defined by claim 1, further comprising at least one devolatilization step carried out after the hydrosilylation and in the presence of at least one inorganic non-nucleophilic base.

4. The process as defined by claim 3, wherein during the hydrosilylation or the devolatilization, an amount of inorganic non-nucleophilic base ranging from 1 to 10,000 ppm, relative to the total mass of synthon and of organosilicon compound, is present.

5. The process as defined by claim 1, said at least one synthon comprising at least one hydrocarbon-based ring member including an oxygen heteroatom and having one of the following formulae:

(1)

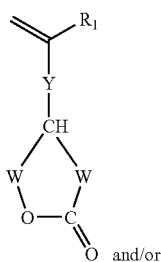
(I)

and/or

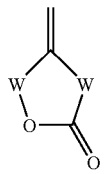
(II)

in which:
the symbols W are identical or different and correspond to a divalent hydrocarbon-based radical selected from among linear or branched alkylene radicals having from 1 to 12 carbon atoms, with the proviso that one of the symbols W may be a free valency;
the symbol Y corresponds to a free valency or a divalent radical selected from among linear or branched alkylene radicals having from 1 to 12 carbon atoms and optionally containing a hetero atom;
the symbol $R_1$ corresponds to a hydrogen atom or a monovalent hydrocarbon-based radical selected from among linear or branched alkyl radicals having from 1 to 12 carbon atoms;

(2)

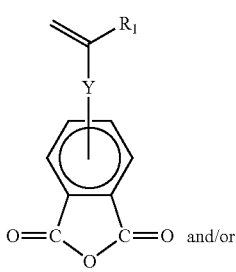
(III)

and/or

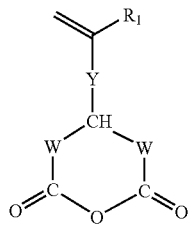
(IV)

in which:
the symbols W are identical or different and correspond to a divalent hydrocarbon-based radical selected from among linear or branched alkylene radicals having from 1 to 12 carbon atoms, with the proviso that one of the symbols W may be a free valency;
the symbol Y corresponds to a free valency or divalent radical selected from among linear or branched alkylene radicals having from 1 to 12 carbon atoms and optionally containing a hetero atom;
the symbol $R_1$ corresponds to a hydrogen atom or a monovalent hydrocarbon-based radical selected from among linear or branched alkyl radicals having from 1 to 12 carbon atoms;

(3)

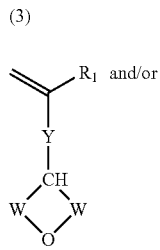
(V)

and/or

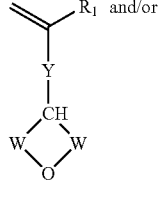
(VI)

in which
the symbols W are identical or different and correspond to a divalent hydrocarbon-based radical selected from among linear or branched alkylene radicals having from 1 to 12 carbon atoms and optionally containing at least one hydroxyl function; with the proviso that one of the symbols W may be a free valency for (V) and the two symbols W can simultaneously be a free valency for (VI);
the symbols W' are identical or different and correspond to a divalent hydrocarbon-based radical selected from among linear or branched alkylene radicals having from 1 to 12 carbon atoms; with the proviso that one of the symbols W' may be a free valency;

the symbol Y corresponds to a free valency or a divalent radical selected from among linear or branched alkylene radicals having from 1 to 12 carbon atoms and optionally containing a hetero atom;

the symbol $R_1$ corresponds to a hydrogen atom or a monovalent hydrocarbon-based radical selected from among linear or branched alkyl radicals having from 1 to 12 carbon atoms;

and (4)

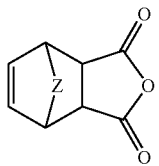
(VII)

in which:

the symbols W are identical or different and correspond to a free valency and a divalent hydrocarbon-based radical selected from among linear or branched alkylene radicals having from 1 to 2 carbon atoms;

the symbol Z corresponds to a divalent radical selected from a carbon atom or a hetero atom.

6. The process as defined by claim 1, said at least one organosilicon compound containing ≡SiH units comprising an epoxidized silane or an epoxidized polyorganosiloxane (POS).

7. The process as defined by claim 6, said at least one organosilicon compound containing ≡SiH units comprising an epoxidized polyorganosiloxane (POS) formed by a linear or cyclic silicone oil having the average formulae:

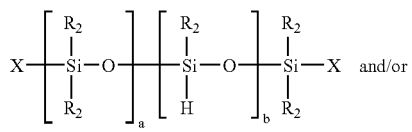
(XVI)

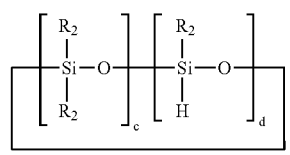
(XVII)

in which the symbols $R_2$ are identical or different and correspond to a monovalent hydrocarbon-based radical selected from among the phenyl radical and linear or branched alkyl radicals having from 1 to 6 carbon atoms;

the symbols X are identical or different and correspond to a monovalent radical selected from among $R_2$, a hydrogen atom, a methoxy radical and an ethoxy radical;

a and b are integers or fractions, such that:

$0 < a \leq 200$, $0 < b \leq 200$, and at least one of the two X corresponding to hydrogen if b=0, $5 < a+b \leq 200$;

c and d are integers or fractions, such that:

$0 < c < 5$, $1 < d < 10$, $3 < a+b < 10$.

8. The process as defined by claim 1, the amount of said at least one metal ranging from 0.1% to 5% relative to the weight of the inert support.

9. The process as defined by claim 1, the amount of said at least one metal of the catalytic composition ranging from 1 to 1,000 ppm relative to the weight of the organosilicone compound.

10. The process as defined by claim 1, said at least one metal of the catalytic composition comprising platinum.

11. The process as defined by claim 1, said inert support comprising carbon black, charcoal, alumina, barium silicate or barium oxide.

12. The process as defined by claim 7, for hydrosilylating a silicone oil with a synthon, comprising the following steps:

a) the synthon is introduced into a reaction medium;

b) an amount of 5 to 5,000 ppm, of heterogeneous catalytic composition, relative to the total mass of the reagents, is introduced under inert gas into the reaction medium;

c) water is optionally introduced into the reaction medium;

d) the inorganic non-nucleophilic base is introduced into the reaction medium; with the proviso that the steps a, b, c and d are carried out in this order or in no particular order;

e) said medium is heated to a temperature of from 25° C. to 200° C.;

f) the silicone oil is then introduced over a period of up to 24 hours, the synthon/silicone molar ratio ranging from 1 to 5;

g) the reaction mass is then filtered to separate the heterogeneous catalytic composition and the functionalized silicone oil;

h) the functionalized silicone oil is then devolatilized in the presence of an inorganic non-nucleophilic base that may be identical to or different from that indicated above; and i) the reaction mass is lastly subjected to at least one operation to remove the solid residues from the reaction medium and the functionalized silicone oil is recovered.

13. The process as defined by claim 7, wherein the silicone oil and the synthon react in the reaction medium in the absence of solvent.

* * * * *